US009814798B2

(12) United States Patent
Cordeiro Bastos et al.

(10) Patent No.: US 9,814,798 B2
(45) Date of Patent: Nov. 14, 2017

(54) YARNS, FIBERS OR FILAMENTS, TEXTILE ARTICLE, AND MEDICAL DEVICE OBTAINED FROM SAID YARNS FOR SKIN CICATRIZATION

(75) Inventors: Tarcis Cordeiro Bastos, Vila Mariana (BR); Gabriel Gorescu, Santo André (BR); Thomas Canova, Indaiatuba (BR)

(73) Assignee: Rhodia Poliamida E Especialidades LTDA, Sao Paulo (BR)

( * ) Notice: Subject to any disclaimer, the term of this patent is extended or adjusted under 35 U.S.C. 154(b) by 79 days.

(21) Appl. No.: 14/116,778

(22) PCT Filed: May 16, 2012

(86) PCT No.: PCT/IB2012/000954

§ 371 (c)(1), (2), (4) Date: Nov. 11, 2013

(87) PCT Pub. No.: WO2012/156805

PCT Pub. Date: Nov. 22, 2012

(65) Prior Publication Data

US 2014/0065092 A1 Mar. 6, 2014

(30) Foreign Application Priority Data

May 18, 2011 (FR) ..................................... 11 54333

(51) Int. Cl.

| | |
|---|---|
| ***A61K 9/00*** | (2006.01) |
| ***A61L 15/22*** | (2006.01) |
| ***A61L 15/18*** | (2006.01) |
| ***A61L 17/04*** | (2006.01) |
| ***D01F 1/10*** | (2006.01) |
| ***D01F 6/60*** | (2006.01) |

(52) U.S. Cl.

CPC ............... *A61L 15/22* (2013.01); *A61L 15/18* (2013.01); *A61L 17/04* (2013.01); *D01F 1/10* (2013.01); *D01F 6/60* (2013.01)

(58) Field of Classification Search

CPC ...................................................... A61L 15/22

See application file for complete search history.

(56) References Cited

U.S. PATENT DOCUMENTS

| | | | | |
|---|---|---|---|---|
| 6,004,588 | A | 12/1999 | Torii et al. | |
| 2011/0059037 | A1 * | 3/2011 | Canova ................ | A61K 9/0014 424/78.03 |
| 2011/0190443 | A1 | 8/2011 | Hideki Di Petta et al. | |

FOREIGN PATENT DOCUMENTS

| | | | |
|---|---|---|---|
| CN | 1506026 | A | 6/2004 |
| JP | 2004131453 | A | 4/2004 |
| WO | WO 2009/077834 | A2 | 6/2009 |
| WO | WO 2010/013107 | A1 | 2/2010 |
| WO | WO 2012/069902 | A1 | 5/2012 |

OTHER PUBLICATIONS

WPI/Thomson—Database WPI—Week 200432; Thomson Scientific, London, GB; AN 2004-344767; XP002665573 & JP 2004 131453 A (Graffiti Twenty One KK) 2004 (3 pgs.).

WPI/Thomson—Database WPI—Week 200476; Thomson Scientific, London, GB; AN 2004-767175; XP002665574 & CN 1506026 A (Zhengzhou Shidai Nano Biotechnology (CO) 2004 (1 pg.).

Wang et al.—"Surface modification of superfine tourmaline powder with titanate coupling agent", 2006, Colloid and Polymer, vol. 12, pp. 1465-1470 (6 pgs.).

Wang et al.—"Influence of tourmaline on negative air ion emitting property of poly(ethylene terephthalate)" 2006, Journal of Macromolecular Science, Part A: Pure and Applied Chemistry, vol. 43. pp. 1749-1756 (8 pgs.).

Carlson & Longaker—"The fibroblast-populated collagen matrix as a model of wound healing: a review of the evidence", Mar.-Apr. 2004, *Wound Repair and Regeneration*, vol. 12(2), pp. 134-147 (14 pgs.).

U.S. Appl. No. 12/747,631, filed Aug. 19, 2010, Thomas Canova, et al.

U.S. Appl. No. 13/717,415, filed Dec. 17, 2012, Thomas Canova, et al.

U.S. Appl. No. 13/717,321, filed Dec. 17, 2012, Thomas Canova, et al.

U.S. Appl. No. 13/056,410, filed Apr. 22, 2011, Daniel Hideki Di Petta, et al.

U.S. Appl. No. 13/989,386, filed May 23, 2013, Gabriel Gorescu, et al.

* cited by examiner

*Primary Examiner* — Paul Dickinson

(57) ABSTRACT

The subject of the present invention is yarns, fibers or filaments and also a textile article and a medical device obtained from said yarns, for improving skin cicatrization, in particular by activating collagen synthesis at the surface of the injured skin. The yarns, fibers or filaments of the invention comprise a polymeric matrix and inorganic fillers, uniformly dispersed in the polymeric matrix, having properties of absorption and/or of emission in the 2-20 μm far-infrared region.

9 Claims, No Drawings

YARNS, FIBERS OR FILAMENTS, TEXTILE ARTICLE, AND MEDICAL DEVICE OBTAINED FROM SAID YARNS FOR SKIN CICATRIZATION

The present application is a U.S. national stage entry under 35 U.S.C. §371 of International Application No. PCT/IB2012/000954 filed May 16, 2012, which claims priority to French Application No. FR 11.54333 filed on May 18, 2011, the whole content of this application being herein incorporated by reference for all purposes.

The subject of the present invention is yarns, fibers or filaments and also textile articles and medical devices obtained from said yarns for improving skin cicatrization, in particular through stimulating the functioning of keratinocytes and fibroblasts, inter alia, by activating collagen synthesis at the surface of the injured skin.

Human skin consists of three superimposed tissues: the epidermis, which is the outermost tissue, the dermis, and the hypodermis, which is the deepest tissue.

Natural human epidermis is composed mainly of three types of cells, which are the keratinocytes, which are very predominant, the melanocytes and the Langerhans cells. Each of these cell types contributes, by virtue of its own functions, to the essential role played in the organism by the skin.

The dermis provides the epidermis with a solid support. It is also its feeder element since it contains a vascularization which the epidermis does not contain. It consists mainly of fibroblasts and of an extracellular matrix, itself composed of various extracellular proteins, among which are in particular collagen fibers, elastin and various glycoproteins.

The hypodermis, which invaginates into the dermis and is attached to the overlying dermis via collagen and elastin fibers, consists essentially of a type of cells that are specialized in fat accumulation and storage, the adipocytes. It is the energy store of the organism. Adipocytes are mature cells that result from a process of differentiation of fibroblasts into pre-adipocytes and adipocytes; this process is called adipogenesis and/or adipocyte differentiation.

Collagen is the principal extracellular matrix (ECM) protein and is the protein that is most abundant in mammals, comprising 25% of the total proteins and 70% to 80% of the skin (dry weight). Collagen acts as a structural scaffold in the tissues. The principal characteristic of all collagen molecules is their rigidity due to the three-stranded helical structure. Collagen types I, II and III are the principal types of collagen present in connective tissues and constitute 90% of all the collagen in the body.

The biosynthesis of collagen begins in the endoplasmic reticulum, where polypeptide chains are synthesized. These polypeptides pass through the endoplasmic reticulum of the fibroblasts which synthesize the proline and lysine residues that are hydroxylated and glycosylated. The conformation of the polypeptides in triple helix form, called "procollagen", follows. The procollagen molecules then pass through the Golgi apparatus, where they are encapsulated in secretory granules and secreted to the extracellular space in the connective tissue. Then, after having been excreted, the procollagen, under the action of extracellular enzymes, undergoes cleavage of the non-helical domains, which results in the collagen molecule. The collagen molecules then organize spontaneously into fibrils. Finally, after the action of the extracellular lysyl oxidase enzyme, the fibrils spontaneously form the reticulum.

The skin can suffer lesions or wounds. The lesion may be of several types; it is, for example, the result of a mechanical trauma (cut, contusion, laceration, graze, bite), thermal trauma (burn), electrical trauma (electrocution) or chemical trauma (burn).

It may also be a question of wounds caused, for example, by venous ulcers (in diabetic individuals for example, or which are post-thrombotic or linked to a chronic venous insufficiency) or decubitus ulcers.

Collagen is a key component in wound healing, which is a complex process, that can be divided up into five phases:

1. Blood Coagulation (Haemostasis)

The blood vessels are the structures most likely to be damaged in the event of an injury. The first objective of the body's repair process consists in stopping bleeding. Platelet aggregation and activation of the coagulation cascade cause the blood to coagulate. The blood platelets release aA-granules, which release several growth factors (FG) and cytokines, which "attract" a variety of inflammatory cells (neutrophils, eosinophils and monocytes) to the site of the wound and initiate the inflammatory phase.

2. Exudation/Inflammatory Phase

During this phase, the dilation of the vessels located close to the wound leads to a serous flow, which causes wound cedema. This liquid, called the exudate, contains a variety of essential substances, such as enzymes, antibodies and inflammatory cells, which are all necessary for the healing process. The inflammatory cells secrete proteolytic enzymes, in particular the neutrophils, the eosinophils and the macrophages. The action of proteolytic enzymes on the macromolecular constituents of the ECM (such as collagen) gives rise to numerous peptides (protein fragments) during wound cicatrization. These degradation products have a chemotactic effect in the recruitment of other cells, such as mononuclear cells, additional neutrophils, and macrophages. The activated macrophages secrete TNF-$\alpha$, which, inter alia, induces the macrophages to produce IL-1b($\beta$). These compounds, TNF-$\alpha$ and IL-1b($\beta$), are the key to the pro-inflammatory cytokines which directly influence collagen formation in the wound by stimulating collagen synthesis by the fibroblasts. The inflammatory cells also secrete growth factors which continue to stimulate the migration of fibroblasts, epithelial cells and vascular endothelial cells into the wound. Consequently, the cellularity of the wound increases.

3. Granulation Phase

The regeneration of new cells, in order to replace the damaged tissue, predominates during the next healing phase. The new tissue is called granulation tissue. It fills the wound from below and has a bright red appearance. The construction of the new tissue is carried out by the fibroblasts (the principal cells of the dermis) through the synthesis of collagen fibers which form the matrix of the connective tissue. During this phase, there are fibroblasts, vascular endothelial cells and also keratinocytes. The vascular endothelial cells secrete a variety of FGs which promote angiogenesis. Granulation is achieved through vascularisation of the ECM.

4. Re-epithelialisation Phase

While the new vessels are responsible for transporting nutritive substances to the regenerated zone, the granulation tissue fills the wound and creates the re-epithelialisation base: the construction of a new layer of skin. Re-epithelialisation of the wound completes the healing process. The epithelial cells divide and migrate from the edges of the wound and close it up. Once the epithelium under the scab is renewed, the scab detaches and the new pinkish epithelial tissue located below becomes visible.

5. Maturation Phase

The wound re-epithelialisation phase is followed by the maturation phase during which the collagen fibers are reorganized so as to give the skin greater strength. However, the new tissue is not identical to the original tissue; it is sometimes uneven and less elastic. In addition, considerable color variations are possible and, in up to 15% of injuries, the formation of a hypertrophic scar can be observed. The scar tissue remodeling process can last years.

In order to protect wounds against external elements during cicatrization, it is known practice to use dressings.

There are many existing types of dressings, which vary depending on the nature of the wounds. One of the most common forms of dressing is a thin compress kept on the wound by an adhesive. The semi-permeable adhesive film makes it possible to allow air and water vapor to pass through. It is very flexible and can be used on joints, for example. It can be combined with a layer of hydrocolloid or alginate gel, or with a hydrogel, allowing better hydration of the wound and preferential cicatrization. The gel may be impregnated with certain products such as antiseptics or corticosteroids in order to limit infections or inflammation of the wound.

The dressings use fibers, for example in the form of a textile.

A large variety of fibers can be used for producing textile materials, for various applications such as, for example, clothing.

For the production of textile materials, the fibers must have certain properties such as, for example, toughness, elasticity, ability to be spun, etc. However, not all fibers are suitable for the production of products for medical use.

Indeed, fibers for medical use must also have properties such as non-toxicity, being sterilizable, having good biocompatibility, biodegradability, good absorbability, and having a soft feel. The term "textiles for medical use" is intended to mean non-implantable devices, implantable devices, extracorporeal devices, health care products and hygiene products. Dressings are considered to be non-implantable devices.

Despite the numerous products currently present on the market there is still a need to provide new solutions for promoting wound cicatrization.

One of the objectives of the present invention is therefore to provide a new, very effective product for improving the wound cicatrization process.

In the cosmetics field, application WO 2009/077834 describes textile articles based on polymers containing additives that have properties of emission and/or absorption in the infrared region, which make it possible in particular to promote the elimination of cellulite. These additives are incorporated into polymeric, in particular polyamide-based, compositions which are then spun in order to form "active" fibers that can be used, for example, for designing textile articles for reducing cellulite.

After lengthy research, the inventors have discovered that yarns, fibers or filaments made of polymer, which have a capacity for emission and/or absorption of infrared radiation in the wavelength range located between 2 μm and 20 μm, make it possible to improve skin cicatrization, in particular by the activation of collagen synthesis.

The yarns, fibers or filaments according to the invention make it possible to improve the proliferation of the fibroblasts and keratinocytes, as well as their migration.

In particular, the yarns, fibers or filaments according to the invention make it possible to improve both the cicatrization process (in particular the speed and effectiveness) and the quality of the cicatrization.

More specifically, the invention relates to yarns, fibers or filaments comprising a polymeric matrix and inorganic fillers which are uniformly dispersed in the polymeric matrix and have properties of absorption and/or emission in the far-infrared region ranging from 2 μm to 20 μm, for improving skin cicatrization.

The present invention is also directed towards a textile article comprising yarns, fibers or filaments of the invention, for improving skin cicatrization.

Another subject of the present invention is a nonimplantable medical device, such as a dressing or a suture thread, comprising yarns, fibers or filaments according to the invention.

A subject of the present invention is also a method for improving skin cicatrization, using the yarns, fibers or filaments, the textile articles or the non-implantable medical devices as described in the present application. This method consists in particular in bringing skin exhibiting one or more lesions into contact with yarns, fibers or filaments, a textile article or a non-implantable medical device according to the invention.

The invention uses yarns, fibers or filaments comprising a polymeric matrix.

The polymeric matrix can be chosen from the group comprising polyesters, polyolefins, polymers based on a cellulose ester such as cellulose acetate, cellulose propionate, rayon, viscose and the polymers of the same family, acrylic polymers and copolymers, polyamides, poly(hexamethylene adipamide) (PA66) or polycaproamide (PA6), or copolymers thereof in any proportions, or else blends between any polymers mentioned above.

According to one preferential embodiment, the polymeric matrix is based on polyamide, chosen from polyamide 6 and polyamide 66 and copolymers of polyamide 6/polyamide 66 in any proportions.

The yarns, fibers or filaments according to the invention comprise inorganic fillers which have properties of absorption and/or emission in the far-infrared region ranging from 2 to 20 μm. Preferably, the inorganic fillers have properties of absorption and/or emission in the far-infrared region ranging from 3 to 20 μm, and even more preferentially from 3 to 15 μm.

According to the invention, the inorganic fillers are dispersed uniformly in the polymeric matrix. The term "dispersed uniformly" is intended to mean that the inorganic fillers are homogeneously incorporated actually within the polymer, in particular that they were incorporated during the synthesis of the polymer or melt-incorporated into the polymer during the spinning phase, or incorporated by means of a concentrate of particles in the form of a masterbatch. They are not inorganic fillers deposited in the form of a coating at the surface of the yarns.

The yarns, fibers or filaments according to the invention comprise inorganic fillers which have properties of absorption and/or emission in the far-infrared region ranging from 2 to 20 μm, that is to say, at least two types of inorganic fillers having such properties are present in said yarns, fibers or filaments. More preferably, at least three types of inorganic fillers having such properties are present in said yarns, fibers or filaments.

The inorganic fillers can be chosen from oxides, sulfates, carbonates, phosphates and silicates.

Preferably, the oxide is chosen from titanium dioxide, silicon dioxide and magnesium oxide.

The sulfate can be chosen from alkali metal or alkaline-earth metal sulfates, preferably from barium sulfate, calcium sulfate and strontium sulfate.

The carbonate is advantageously chosen from calcium carbonate or sodium carbonate.

Preferably, the silicate is chosen from actinolite, tourmaline, serpentine and kaolin.

The phosphate can be chosen from zirconium phosphates, apatite or mixtures thereof.

According to one advantageous embodiment of the invention, the inorganic fillers are chosen from oxides, sulfates, carbonates, phosphates and silicates.

Preferably, the yarns, fibers or filaments of the invention contain at least two types of inorganic fillers chosen from the following types: oxides, sulfates, carbonates, phosphates and silicates.

Particularly advantageously, the fibers or filaments of the invention contain at least two inorganic fillers of different types, preferably at least three inorganic fillers of different types, chosen from the following types: oxides, sulfates and silicates.

According to one embodiment of the invention, the yarns, fibers or filaments of the invention contain three different inorganic fillers, the three fillers being an oxide, a sulfate and a silicate.

According to one advantageous embodiment of the invention, the yarns, fibers or filaments of the invention contain at least two inorganic fillers chosen from titanium dioxide, an alkali metal or alkaline-earth metal sulfate, and a silicate.

Preferably, at least two inorganic fillers chosen from titanium dioxide, barium sulfate and tourmaline are present in the yarns, fibers or filaments of the invention.

Particularly advantageously, the yarns, fibers or filaments of the invention comprise three inorganic fillers of different types. The combination of the three inorganic fillers is preferably the titanium dioxide/alkaline-earth metal sulfate/silicate combination; preferably titanium dioxide/barium sulfate/tourmaline.

In this case, the proportion by weight of the three inorganic fillers is preferably between 80:10:10 and 10:30:60, and more specifically in a proportion of 50:25:25.

According to another, also advantageous, embodiment, the yarns, fibers or filaments contain at least two inorganic fillers of different types, preferably at least three inorganic fillers of different types, chosen from the following types: oxides, phosphates and silicates.

In this embodiment, particular preference is given to the combinations of three inorganic fillers of different types, the three fillers being an oxide, a phosphate and a silicate.

According to one embodiment of the invention, the proportion by weight of the combination of inorganic fillers relative to the total weight of the polymeric composition (matrix+fillers) is greater than 1.0%, preferably greater than or equal to 1.5% and even more preferentially greater than or equal to 2.5%.

Preferably, the proportion by weight of the combination of inorganic fillers relative to the total weight of the polymeric composition is less than 9%, preferably less than 6%, advantageously less than 4.5%.

The inorganic fillers according to the invention are in the form of particles, which advantageously have a weight-average size of less than or equal to 2 μm, measured according to the laser diffraction particle size analysis method (using, for example, Malvern or Cilas particle size analyzers).

It is preferable for the inorganic fillers used in the present invention to have a particle size which is neither too small, so as to prevent any risk of the particles leaving the polymeric matrix and being introduced into the wounds and penetrating into the human body or dispersing in the environment, nor too large, which would make the incorporation of the particles into the polymeric matrix more difficult and would make the material more abrasive on contact with the skin, which could prove to be harmful to the cicatrization process.

Thus, the inorganic fillers according to the invention are in the form of particles which advantageously have a weight-average size, measured according to the laser diffraction particle size analysis method, ranging from 0.1 to 2 μm, and more preferentially from 0.2 to 1.5 μm.

The inorganic fillers advantageously have a particle size distribution with 99% by weight of the particles having a size of less than 1.0 μm, preferably 90% by weight of the particles having a size of less than 0.5 μm. The particle size distribution is also measured by the laser diffraction particle size analysis method (using, for example, Malvern or Cilas particle size analyzers).

Furthermore, the ratio between the size of particles of the inorganic fillers and the diameter of the filament is advantageously optimized so as to avoid the problems described above.

The ratio between the average equivalent diameter of the filaments according to the invention and the weight-average size of the inorganic fillers, measured according to the laser diffraction particle size analysis method, is advantageously greater than or equal to 10. This ratio between the average equivalent diameter of the filament and the weight-average size of the inorganic fillers is preferably less than or equal to 200.

The yarns, fibers or filaments according to the invention are characterized in that the filaments preferably have a linear mass (titer) ranging from 0.2 to 20 dtex, advantageously from 0.5 to 8 dtex, and even more preferentially from 0.5 to 3.5 dtex.

The titer of the filaments can vary according to the application chosen. Indeed, for an application of the "dressing" type, the filaments advantageously have a titer ranging from 0.5 to 1.5 dtex, whereas, for applications for compression garments of the "postoperative" type, the filaments can have a titer ranging from 2 to 8 dtex.

The filaments according to the invention preferably have an average equivalent diameter ranging from 4 to 50 μm, preferably from 6 to 30 μm.

Thus, particularly preferably, when the average diameter of the filament ranges from 4 to 20 μm, the inorganic fillers are in the form of particles having a weight-average size, measured according to the laser diffraction particle size analysis method, ranging from 0.1 μm to 0.4 μm, and more preferentially from 0.2 μm to 0.4 μm.

Thus, when the average diameter of the filament ranges from 20 to 50 μm, the inorganic fillers are advantageously in the form of particles having a weight-average size, measured according to the laser diffraction particle size analysis method, ranging from 0.25 μm to 2 μm, and more preferentially from 1 to 2 μm.

As explained above, the inorganic fillers are incorporated during the polymer synthesis phase, or by direct mixing with the polymer during the filament spinning phase, or else by means of a concentrate of particles in the form of a masterbatch, it being possible for the latter to be subsequently diluted to predetermined concentrations in the polymeric mass during the spinning phase.

The yarns, fibers or filaments according to the invention preferably have more than 10 infrared radiation absorption peaks in the following ten frequency ranges: 3.00+/−0.30 μm, 6.20+/−0.50 μm, 8.00+/−0.25 μm, 8.50+/−0.25 μm, 9.00+/−0.25 μm, 9.50+/−0.25 μm, 10.00+/−0.25 μm, 10.50+/−0.25 μm, 11.00+/−0.25 μm, 14.60+/−2.10 μm, at least one peak being present in at least seven of these ten frequency ranges.

The infrared radiation absorption spectrum can be determined by any method known to those skilled in the art. One possible method is the use of a Bruker Equinox 55 apparatus, with a resolution of 4 $cm^{-1}$. In this case, the spectrum obtained is in ATR (Attenuated Total Reflectance) form, using a ZnSe crystal.

The yarns, fibers or filaments according to the invention can advantageously have additional functionalities, different from the functionality of emission/absorption in the far-infrared (FIR). They may in particular be yarns, fibers or filaments which combine the FIR functionality with one or more of the functionalities below:

- moisture regulation,
- protection against micro-organisms,
- hydrophobicity/hydrophilicity,
- capacity for absorption/capillarity,
- anti-odor,
- antifungal,
- insect repellent,
- protection against UV rays,
- anti-staining.

These additional functionalities can be provided by additives/active agents, added to the yarn, fiber or filament according to the invention during its preparation.

The process for obtaining such fibers according to the invention can consist in preparing one or more suspensions of inorganic fillers such as, for example, a silicate, titanium dioxide and an alkali metal or alkaline-earth metal sulfate, stabilized with surfactants. The suspension(s) is(are) then added to the synthesis of the polyamide. An alternative is to introduce a part of the inorganic fillers, previously made into the form of a masterbatch, into the molten polymer at the time of the spinning. The polyamide obtained is cooled, cut up and remelted before passing through an extruder so as to form the yarn.

By virtue of this process for example, the polyamide yarns, fibers or filaments according to the invention contain the inorganic fillers in a manner uniformly dispersed in the polymer matrix.

In the case of fibers obtained by spinning in the molten state, the inorganic fillers can be introduced into the molten polymer by means of a mixing device, for example upstream of a spinning device. Through the spinning of the filler-loaded polymer composition, it is possible to obtain continuous multifilament yarns, monofilaments, short and long fibers, or mixtures thereof. All the yarns, fibers and filaments that can be obtained by spinning will be called “yarns”. The yarns obtained from the filler-loaded polymeric compositions presented above can be subjected to all the textile treatments known to those skilled in the art, such as extrusion, drawing out, texturing, dyeing, finishing, etc.

The textile article can be obtained from a single type of yarn, fiber or filament according to the invention, or from a mixture of yarns, fibers or filaments according to the invention with yarns, fibers or filaments other than those of the invention. The yarns, fibers or filaments other than those of the invention can advantageously have functionalities which are different from and/or complementary to the functionality of emission/absorption in the far-infrared (FIR). They may in particular be yarns, fibers or filaments with one or more of the functionalities below:

- moisture regulation,
- antimicrobial protection,
- hydrophobicity or hydrophilicity,
- capacity for water absorption/capillarity,
- anti-odor,
- antifungal,
- insect repellent,
- protection against UV rays,
- anti-adhesive.

These functionalities can be provided by additives/active agents, added to the yarns, fibers or filaments other than those of the invention during their preparation.

The term “textile article” is intended to mean in particular a fabric, a knit or a nonwoven.

The textile article is produced by known techniques using the yarns, fibers or filaments of the invention as raw material, and optionally other natural (for example cotton) yarns, fibers or filaments or synthetic (for example viscose) yarns, fibers or filaments. These additional yarns, fibers or filaments can in particular have good hygroscopicity, which can be advantageous in the application.

According to one particularly advantageous embodiment, the textile article is in the form of a bandage or a garment, such as, for example, bermuda shorts, a t-shirt, a pair of tights, trousers, a support stocking or a postoperative compression garment (of the type of those used in conventional or plastic surgery).

The non-implantable medical device is in particular a dressing or a suture thread. The dressing may be a gauze, a sticking dressing, a plaster, a bandage such as a compression bandage or an absorbent bandage, adhesive tape or a scaffold tissue support.

The non-implantable medical device according to the invention comprises the yarns, fibers or filaments defined above, for example in the form of textile articles such as gauzes. It may also involve a combination of the yarns, fibers, filaments or textile articles of the invention with other textile bases (for example, nonwoven felts or tricots) or with plastics. The non-implantable medical device can also comprise a combination of the yarns, fibers, filaments and textile articles and combinations thereof with other textile or plastic bases:

- with other fibers, such as alginate fibers, chitosan fibers, chitin fibers or collagen fibers, etc., and/or
- with medicaments for improving or accelerating the wound healing process.

The interaction between the yarns, fibers or filaments and the skin improves the cicatrization of the injured skin, in particular by stimulating collagen synthesis. The lesion may be of several types; can be, for example, the result of a mechanical trauma (cut, contusion, laceration, graze, bite), thermal trauma (burn), electrical trauma (electrocution) or chemical trauma (burn).

Preferably, the method according to the invention consists in applying the yarns, fibers, filaments, textile article or non-implantable medical device against the injured part of the skin, which is optionally disinfected beforehand.

The recommended application may range from a few hours to several days depending on the seriousness, the type and the depth of the lesion.

According to the invention, and particularly advantageously, the yarns, fibers, filaments, textile article or non-implantable medical device may be sterilized before use thereof.

Surprisingly, the invention makes it possible to obtain highly effective cicatrization.

The present invention also has the advantage that the inorganic fillers of the textile article are highly resistant to washing/cleaning, through the incorporation of these fillers into the polymeric matrix.

Exemplary embodiments of the invention are given hereinafter. These examples are given by way of illustration and are not limiting in nature.

EXAMPLES

Example 1

1. Polymeric Composition Preparation

A masterbatch of polyamide 66 is prepared by incorporating 20% by weight of infrared-emitting inorganic fillers in powder form into polyamide 66 with a relative viscosity (VR) of 43, measured in a solution of formic acid at 90% in water.

The resulting masterbatch is extruded, cooled and granulated.

The resulting granules are remelted and then introduced during spinning into molten polyamide 66 with a relative viscosity (VR) of 43, measured in a solution of formic acid at 90% in water, in a proportion which makes it possible to obtain the desired amount of inorganic fillers in the polymer matrix.

2. Polymer Spinning and Fabric Preparation

The molten polymeric composition obtained is spun at a temperature of between 280° C. and 300° C. (measured in the die), air-cooled (20° C., relative humidity of 65%) and wound at a speed of 4200 m/min so as to obtain a continuous multifilament yarn. The multifilament yarn made up of 68 filaments with a circular cross section was subsequently textured. The titer of the filament in the final product is 1.2 dtex.

In the example of the invention, a yarn of polyamide 66 containing 1.5% by weight of $TiO_2$ with a weight-average particle size of 0.3 μm, 0.5% by weight of $BaSO_4$ with a weight-average particle size of 0.25 μm and 0.2% by weight of tourmaline with a weight-average particle size of 0.3 μm was prepared.

The resulting yarn is then converted into knits using a circular knitting machine.

By way of comparison, a multifilament yarn was also prepared from a virgin polyamide 66 (containing only 1.5% by weight of $TiO_2$ with a weight-average particle size of 0.3 μm) with a relative viscosity (VR) of 43, measured in a solution of formic acid at 90% in water. The comparative yarn is also made up of 68 filaments with a circular cross section and was subsequently textured. The titer of the filament in the final product is 1.2 dtex. The resulting yarn is also converted into knits using the same circular knitting machine.

Bermuda shorts were subsequently produced from said knits. The bermuda shorts have a surface density of 305 $g/m^2$, and contain 12% of spandex. These articles were subsequently used to evaluate the effectiveness in the application envisaged (cf. in vivo tests below).

3. In Vitro Tests:

In order to evaluate the effect due to the presence of the fabric according to the invention on collagen synthesis, an in vitro method which was described in the literature (Carlson, M A, Longaker, M T. *Wound Repair and Regeneration,* 12(2):134-47, 2004 March-April) and validated by specialists in the field was used. This method consists in using fibroblast-populated collagen matrix (MCFP) as an in vitro experimental model of healing, since this gives a reasonable approximation of wound cicatrization during the established granulation tissue phases.

According to the MCFP model, a solution of collagen type I and of primary fibroblasts is added to a cell culture. This solution polymerizes at physiological pH and at a temperature of 37° C., giving rise to a gel, and then the medium supplemented with growth factors or with serum is added.

The fibroblasts were obtained from the normal skin of five volunteers. The evaluation of the fibroblast samples from each volunteer was carried out eight times. The results given below are an average of these evaluations.

The fibroblasts were maintained under defined temperature and oxygen saturation conditions (37° C. and 5% of $CO_2$) for seven days.

The same model was constructed in the presence of external light. After seven days of culture, the Petri dishes were photographed using the UTSCSA Image Tool for Windows version 3 software, and the surface of each gel was measured, making it possible to calculate the level of contraction of the gel.

The method previously described makes it possible to observe the level of contraction of the gel, which makes it possible to evaluate the collagen synthesis activity by the fibroblasts. Indeed, the greater the contraction of the gel, the greater the collagen synthesis.

The gel contraction results after seven days are described in table 1 below.

TABLE 1

Increase in gel contraction after seven days

| Fabric used | Increase in contraction (relative to a contraction without fabric) |
|---|---|
| Fabric of example 1 | +21% |
| Comparative fabric | +1% |

Conclusion: It is noted that the degree of contraction of the gel, when it is in contact with the fabric of the invention, is much greater than that observed with the comparative fabric. Thus, collagen synthesis is significantly increased in the presence of the fabric of the invention.

4. In Vivo Tests:

In order to evaluate collagen synthesis in vivo, a study was carried out with a group of 15 volunteer women who wore bermuda shorts made with yarn according to the invention for one leg and the comparative polyamide yarn for the other leg.

The bermuda shorts are in direct contact with the skin.

After 60 consecutive days of using the bermuda shorts at a rate of six hours per day, an evaluation of the amount of collagen type I (the most present in the skin) in the skin was set up. The results given below are an average of these evaluations.

Human skin exhibits a maximum level of fluorescence excitation at a wavelength of 295 nm and of fluorescence emission at 360 nm. This fluorescence is attributed to the aromatic side chain of the amino acid tryptophan present in the protein structures of the skin. Another excitation maximum is observed at the wavelength of 340 nm and a fluorescence emission at 400 nm. This other maximum is attributed to the cross-links of collagen type I.

The method chosen is measurement by fluorescence spectroscopy, which makes it possible to quantify the presence of collagen type I in the skin by comparing the amount of tryptophan (reference measured at 360 nm) with the amount of collagen cross-links (measured at 400 nm).

The intensity of the tryptophan signal in the excitation spectrum at 295 nm is strongly linked to cell proliferation. A reduction in the intensity of the signal at 295 nm indicates a reduction in epidermal proliferation associated with skin aging.

Internal (intrinsic) aging of the skin shows a 10 to 20% reduction in the signal for tryptophan and collagen type I every 10 years.

Taking into account the short duration of the test, the tryptophan signal was considered to be a virtually constant internal reference during the study.

The ratio between the intensities of the signals at 340 nm and 295 nm ($I_{340}/I_{295}$) indicates the increase in the number of collagen type I cross-links, resulting from the increase in the synthesis of this molecule.

The results of the quantification of the collagen synthesis are given in table 2 below.

TABLE 2

| Increase in collagen (%) | |
|---|---|
| Sample | Increase after 60 days |
| Fabric of example 1 | 5.9% |
| Comparative fabric | 0.9% |

The statistical test shows that there is a statistically significant difference between the fabric according to the invention and the comparative fabric from the point of view of the increase in collagen synthesis in vivo ($p<0.0001$).

The above two tests in vitro and in vivo confirm that the contact of the yarn supplemented with additive according to the invention, with the skin, makes it possible to observe a significant increase in collagen synthesis.

As is already commonly accepted by the scientific community, collagen synthesis plays an important role in the skin cicatrization process, and the increase in collagen synthesis contributes significantly to the quality and the speed of cicatrization.

The invention claimed is:

1. A method for improving skin cicatrization, the method comprising applying to the injured part of the skin yarns, fibers or filaments having a linear mass of 1.2 dtex comprising a polymeric matrix, said polymeric matrix being polyamide 66, and particulate inorganic fillers, said particulate inorganic fillers being uniformly dispersed in said polymeric matrix, having a weight average particle size of from 0.2 to 1.5 μm, and having properties of absorption and/or emission in the far-infrared region ranging from 2 μm to 20 μm, thereby improving skin cicatrization;

wherein said yarns, fibers or filaments contain 1.5% by weight titanium dioxide, 0.5% by weight barium sulfate, and 0.2% by weight tourmaline.

2. The method according to claim 1, wherein the yarns, fibers or filaments stimulate collagen synthesis.

3. The method according to claim 1, wherein a textile article comprises said yarns, fibers or filaments.

4. The method according to claim 3, wherein the textile article is a fabric, a knit, or a nonwoven.

5. The method according to claim 4, wherein the textile article is a bandage or a garment.

6. The method according to claim 1, wherein a non-implantable medical device comprises said yarns, fibers or filaments.

7. The method according to claim 6, wherein the non-implantable medical device is a dressing or a suture thread.

8. The method according to claim 1, wherein the particulate inorganic fillers have a particle size distribution wherein 99% by weight of the particles have a size of less than 1.0 μm and 90% by weight of the particles have a size of less than 0.5 μm.

9. The method according to claim 1 wherein the ratio of the average diameter of the filaments to the weight average particle size of the particulate inorganic fillers is greater than 10 and less than 200.

* * * * *